United States Patent [19]

Ramsdell

[11] Patent Number: 4,758,426

[45] Date of Patent: Jul. 19, 1988

[54] THERAPEUTIC TOILET SOLUTION AND METHOD OF DISPERSION

[76] Inventor: Bruce V. Ramsdell, 1256 Druid Knoll Dr., DeKalb County, Ga. 30319

[21] Appl. No.: 61,187

[22] Filed: Jun. 11, 1987

[51] Int. Cl.$^4$ .................. A61K 9/08; A61K 7/035
[52] U.S. Cl. ........................................ 424/69; 514/2; 514/934; 514/937; 514/946; 514/947
[58] Field of Search ............... 424/69; 514/2, 934, 514/937, 946, 947

[56] References Cited

U.S. PATENT DOCUMENTS

| | | | |
|---|---|---|---|
| 2,890,151 | 6/1959 | White | 514/61 |
| 3,278,383 | 10/1966 | White et al. | 424/69 |
| 3,627,871 | 12/1971 | Groves et al. | 514/947 |
| 4,053,582 | 10/1977 | Sticki | 424/89 |
| 4,261,982 | 4/1981 | Luedders et al. | 514/947 |
| 4,424,232 | 1/1984 | Parkinson | 514/468 |
| 4,497,824 | 2/1985 | Schulte | 514/166 |
| 4,512,978 | 4/1985 | Inwood | 514/552 |
| 4,595,591 | 6/1986 | Mardi et al. | 424/127 |
| 4,677,120 | 6/1987 | Parish et al. | 514/425 |

*Primary Examiner*—John Kight
*Assistant Examiner*—S. A. Acquah
*Attorney, Agent, or Firm*—Donald R. Andersen

[57] ABSTRACT

The present invention provides a therapeutic toilet solution effective for the eradication and prevention of skin lesions or warts associated with condylomata acuminata, and a method of dispersion thereof.

5 Claims, No Drawings

THERAPEUTIC TOILET SOLUTION AND METHOD OF DISPERSION

BACKGROUND OF THE INVENTION

This invention relates to the art of chemical compounds and solutions, and methods of dispersion thereof, useful in the field of eradication and prevention of growths or warts caused by condylomata acuminata.

SUMMARY OF THE INVENTION

The eradication and removal of skin growths or warts caused by condylomata acuminata is a problem which has presented difficulty. These growths or warts, commonly known as venereal warts, are associated with the virus condylomata acuminata.

Prior to the present invention, such growths or warts were eradicated and prevented by surgical intervention, application of caustic acid, cryotherapy and cautery. More recently, attempts also have been made to eradicate and prevent such growths or warts using laser technology.

The disadvantages of the prior efforts to eradicate and prevent the growths or warts is that they were painful, exposed the person suffering from the condition to the risk of infection and bleeding, required in some cases local or general anesthesia, and hospitalization. Additionally, such efforts were limited primarily to surface conditions or warts and did not prevent reoccurrence.

Finally, it should be noted that such lesions are suspected of being pre-cancerous in many cases, and the present invention is not intended or believed to have any efficacy in the treatment of cancer. For this reason, any such conditions should be brought to the attention of a physician, in conjunction with the present invention.

It is an object of the present invention to provide a compound or solution which is capable of effectively treating and eliminating growths or warts caused by condylomata acuminata.

It is a further object of the present invention to provide a compound or solution which is capable of easy and thorough dispersion for the purpose of treating and eliminating growths or warts caused by condylomata acuminata.

It is still a further object of the present invention a compound which when applied provides improved exposure and penetration to affected areas.

The foregoing objectives and still other objectives and advantages of the present invention will become apparent upon reading the following specification describing one preferred embodiment of the invention.

DESCRIPTION OF A PREFERRED EMBODIMENT

The preferred embodiment of the present invention includes a compound or solution which is useful in the treatment of skin lesions or warts caused by condylomata acuminata, which lesions or warts are commonly referred to as venereal warts. The compound or solution includes an aqueous solution of super absorbant, antifungal and antibiotic compounds which provides improved therapeutic effects in eliminating and avoiding recurrence of lesions or warts in the treated areas, particularly when used in the prescribed manner for the dispersion of such compound upon application to the affected areas.

The compound or solution comprises at least a superabsorbent compound capable of absorbing excess body moisture and which is believed to be lethal to the organisms associated with condylomata acuminata, and an antifungal compound for treatment of fungi commonly co-existing with the condylomata acuminata, in aqueous solution. While the choice of superabsorbent compounds and antifungal compounds may vary depending upon the application, it has been found that the superabsorbent powder Zeabsorb and the antifungal powder Zeabsorb-AF, both registered trademarks of Stiefel Laboratories and manufactured by Stiefel Laboratories, Coral Gables, Fla., under U.S. Pat. Nos. 2,890,151 and 3,278,383, are suitable when combined in aqueous solution to provide a therapeutic toilet solution which is effective in the eradication and prevention of skin lesions or warts associated with condylomata acuminata.

Additionally, an antibiotic compound also may be a desirable ingredient in the solution preferred herein, in order to further avoid any risk of infection, although such ingredient does not appear to be necessary to achieve the desired effects on eradication and prevention of the skin lesions or warts. A suitable antibiotic compound is Polysporin Polymyxin B-Bacitracin, containing Aerosporin (polymxin B sulfate) and bacitracin zinc, manufactured by Burroughs Wellcome Co., Research Triangle Park, N.C. 27709. Polysporin and Aerosporin are registered trademarks of Burroughs Wellcome Co.

It has been found that an effective solution consists of 35 grams superabsorbent compound and 35 grams antifungal compound, in an aqueous solution of sterile water to produce one liter of solution. Ten grams of antibiotic powder also may be included before adding sterile water.

The aqueous solution is applied liberally in the affected areas and in the adjacent areas by topical application. Before the areas of application have dried, an external source of light to medium blow drying air is directed to the areas of application to assist in the drying process. The process of drying appears to have therapeutic effects with regard to the pathological tissues and the solution appears to be lethal to the causative organisms associated with the condylomata acuminata. The air or blow drying is discontinued within several minutes after the cooling sensation associated with the drying of the solution ceases, indicating that the solution in and around the affected areas has evaporated leaving the powder residue dispersed and deposited thoroughly throughout the affected areas. It is believed that this method of dispersion provides improved distribution and penetration throughout the affected areas. The application should be repeated at least twice each day until the lesions or warts have been eliminated.

From the foregoing description it will be seen that the present invention provides a therapeutic toilet solution and method of dispersion thereof. It will be understood, however, by those skilled in the art that the present invention may be adapted to encompass other embodiments of the invention than the preferred embodiment set forth above, and that the embodiments of the invention described above are merely illustrative, and that the present invention is limited solely by the appended claims.

I claim:

1. A solution for use in eradicating and preventing skin lesions and warts associated with condylomata acuminata, comprising an aqueous solution of antifungal compound and super absorbent compound.

2. A solution for use in eradicating and preventing skin lesions and warts associated with condylomata acuminata as claimed in claim 1, wherein said antifungal compound and said superabsorbent compound are dispersed in aqueous solution in volume sufficient to eliminate and prevent skin lesions or warts associated with condylomata acuminata.

3. A solution for use in eradicating and preventing skin lesions and warts associated with condylomata acuminata as claimed in claim 1, further including an antibiotic compound, wherein said antifungal compound, said superabsorbent compound and said antibiotic compound, are dispersed in aqueous solution in volume sufficient to eliminate and prevent skin lesions and warts associated with condylomata acuminata.

4. A method of dispersion of antifungal and superabsorbent compounds which includes mixing said compounds in an aqueous solution, applying the solution to the affected areas in order to provide substantially complete dispersion of the aqueous solution, and applying low to medium blow drying air to the affected areas to cause substantially complete evaporation of the solution.

5. A method of dispersion as set forth in claim 4, wherein said antifungal compound and said superabsorbent compound are dispersed in aqueous solution in volume sufficient to eliminate and prevent skin lesions or warts associated with condylomata acuminata.

* * * * *